(12) United States Patent
Silva

(10) Patent No.: US 6,308,710 B1
(45) Date of Patent: Oct. 30, 2001

(54) SCROTAL DRAPE AND SUPPORT

(76) Inventor: David Silva, 4798 Dalhousie Pl., Marietta, GA (US) 30068

( * ) Notice: Subject to any disclaimer, the term of this patent is extended or adjusted under 35 U.S.C. 154(b) by 0 days.

(21) Appl. No.: 09/545,374

(22) Filed: Apr. 7, 2000

Related U.S. Application Data

(60) Provisional application No. 60/128,724, filed on Apr. 12, 1999.

(51) Int. Cl.[7] .................................................... A61B 19/00
(52) U.S. Cl. ............................................ 128/849; 128/853
(58) Field of Search ..................................... 128/849–856

(56) References Cited

U.S. PATENT DOCUMENTS 4,690,137 * 9/1987 Starzmann ............................ 128/853
4,807,644 * 2/1989 Sandhaus ............................. 128/853

* cited by examiner

*Primary Examiner*—Michael A. Brown
(74) *Attorney, Agent, or Firm*—Paul M. Denk

(57) ABSTRACT

A generally V-shaped drape formed of polymer or related materials and which functions as a sling to hold the scrotum upwardly, and out of place, during medical analysis and treatment. The drape includes a V-shaped member, formed of a highly flexible polymer, such as polyethylene, and includes a pressure sensitive adhesive area at its lower end, for application to the base of the scrotum, and further includes pressure sensitive adhesive at the upper legs of the V-shaped drape, for application to the abdomen wall, to provide a sling that furnishes continuing clearance for access to and application of the various medical instrumentation used especially during treatment of the prostate, or other proximal anatomy located at this region of the patient.

2 Claims, 1 Drawing Sheet

SCROTAL DRAPE AND SUPPORT

CROSS-REFERENCE TO RELATED APPLICATION

This application is a non-provisional patent application based upon provisional patent application having Ser. No. 60/128,724, filed on Apr. 12, 1999, which is owned by the same inventor.

BACKGROUND OF THE INVENTION

This invention relates to a form of support or sling for elevating the scrotum, so that further medical instrumentation may be arranged in proximity therebelow, and have clearance for performance of other medical testing, or treatment, particularly with respect to the investigation of any infection that may have developed in the vicinity of the prostate.

As in known in the art, various types of instrumentation have been developed for treatment of lower urinary infections, diseases, and even malignancies, and these instrumentations require clear access to the area generally demarcated by the perineum, at the vicinity between the lower genital area, behind the scrotum, and the location of the anus. Such instrumentation is very delicate of a structure, must be precisely located, since specifically this type of instrumentation is used for both locating the exact positioning, and size, of the prostate, and in addition, is applied for taking biopsies at various locations therein, to provide for their testing, screening, and analysis, for malignancy, or not, and in the event that evidence of carcinogenic presence is detected, treatment, such as by seed radiation, may be employed through the usage of a biopsy type of needle or implanting instrument that precisely locates the insertion of the radiation seed at an exactly determined location. During such procedure, though, it is necessary that the area be completed cleared, so that such equipment can be delicately applied, to achieve its intended results.

Obviously, in the medical field, there are a variety of slings, tie means, or the like, that may be used to hold a body organ displaced so that access may be attained to a specific region for medical treatment or surgery.

SUMMARY OF THE INVENTION

It is the principal object of this current invention to provide a drape, formed like a sling, and which can be applied in proximity under the scrotal area, and adhered to the abdomen, in order to elevate these body parts out of the way for locating an application of medical instrumentation, in preparation for performance of a specific medical surgical procedure.

This particular invention relates to a scrotal drape, that is designed for usage in conjunction with a patient, and is applied to lift the scrotum up and out of the way during particularly the radiation seed implanting procedure. Likewise, the sling may be used to lift the scrotum up and displaced out of the way even during initial testing, as when such instrumentation may be used for initially x-raying the suspect area, in the vicinity of the prostate, or when biopsies are taken of the suspect area, in order to determine the presence of cancer, or other medical impairments.

The drape of this invention includes a V-shaped length of preferably polymer material, which may be fabricated of polyethylene, or the like, having a length of approximately 12 to 15 inches, for each individual leg of the V, and an adhesive is applied to the upper ends of each of the fabricated legs of the V-shape, comprising a pressure sensitive type of adhesive, while the bottom of the V, at its base, also includes a location of similar pressure sensitive adhesive, and for the following purposes.

In usage, the drape is applied underneath and behind the scrotum, the pressure sensitive adhesive has a covering removed therefrom, and the lower part of the V-shaped drape member is adhesively applied under the scrotum and adhered thereto. Then, the legs of the V-shaped member are pulled upwardly, upon the surface of the abdomen, until such time as it lifts the scrotum upwardly, so as to add clearance therebelow, and at this time the covering material for the pressure sensitive adhesive, at the upper end of the legs of the V-shape, are removed, and these portions of the drape are then applied by adhesive adherence to the surface of the abdomen, to function as a sling or lift for removal, out of the way, of the specified anatomy as previously reviewed.

While the material identified for usage for fabricating of the drape of this invention have been heretofore described as being of a polymer, it is just as likely that the same could be fabricated of a cloth, or of any other materials, that may function reasonably as a sling-like device, and fabricated of reasonably inexpensive materials, so that the entire device may be disposable, after a single usage.

It is, therefore, the principal object of this invention to provide a patient drape that may be used to lift the scrotum up and out of the way during radiation seed implanting, during treatment of a patient.

Another object of this invention is to provide a scrotal drape that functions to furnish clearance to the medical practitioner while investigating a patient, either by way of x-ray treatment, the undertaking of biopsies, or any other preliminary procedure required incident to a determination of the presence of any malignancy in the patient.

Still another object of this invention is to provide a V-shaped drape that allows access to the area of the penis for cystoscopy, as after radiation seeds are implanted.

Another object of this invention is to provide a drape so fabricated into the configuration of a V-shape, and which may be formed on a clear or semi-translucent material, in order to facilitate its usage.

Another object of this invention is to provide a sterilized drape, that may be individually packaged, but yet be readily disposable after a single usage.

These and other objects may become more apparent to those skilled in the art upon reviewing the summary as provided herein, and upon undertaking a study of the description of its preferred embodiment, in view of the drawing.

DESCRIPTION OF THE PREFERRED EMBODIMENT

Figure 1:
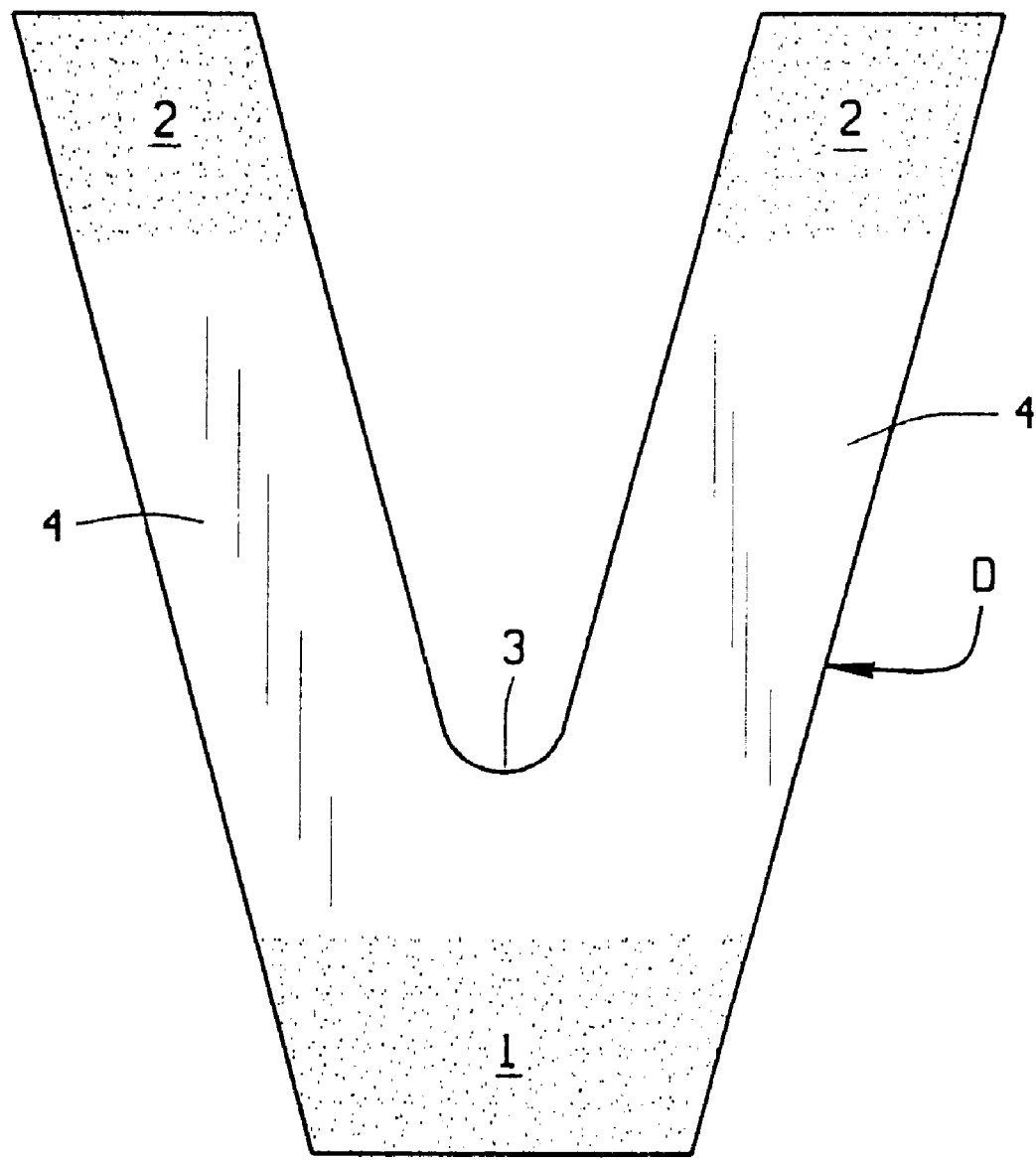
FIG. 1 provides an elevational view of the V-shaped drape of this invention, disclosing the proximate areas where pressure sensitive adhesive are applied thereto.

In referring to the drawing, and its FIG. 1, the drape D of this invention is readily disclosed, it comprises a generally V-shaped sling-like member, fabricated of the materials as previously reviewed, which at its base includes the deposit and application of a pressure sensitive adhesive, as at 1, at its lower portion, and at the upper tab ends of the legs 4 of this embodiment, includes the application of additional pressure sensitive adhesive, as at the regions 2, as noted. Between the legs 4 of the drape, there is a cutout segment, as at 3, which is generally formed upon a radius, and which provides a support at that location for holding the scrotum upwardly, during application of this drape, when applied for usage for medical purposes, as previously explained. Obviously, any type of covering material, such as paper, glassine, or the like, may be applied over the adhesive areas 1 and 2, during manufacture, shipment, and storage, but which may be readily removed, when the drape is being applied for medical analysis and treatment purposes.

During usage of the drape of this invention, the medical assistant will have previously washed and wiped off the proximate area of application of this drape, with any type of skin cleanser, such as betadine, and then the drape is applied into position, under the scrotum, at which time the covering material overlying the adhesive 1 will be removed, allowing that segment of the drape to be applied underneath and behind the scrotum, in preparation for its lift. Then, the legs 4 will be pulled upwardly along the front of the abdomen, of the patient, at which time the covering material overlying the regions of the adhesive 2, will be removed, so that the drape can then be applied and adhered to the abdomen, and thereby obtain the resistance force necessary to allow the drape to be used as a sling for holding the scrotal area displaced, in preparation for medical treatment.

Thus, in performance of the steps of usage of the drape of this invention, the scrotum will have been prepared for application of the drape, and the technician will be assured that the area surrounding the same will be dry and free of most povidone-iodine residue. Then, one peels back the bottom portion of the adhesive area 1, and applies the same to the region of the scrotum, making sure that the drape adheres to and covers most of the lower and back segment of the scrotum in preparation for its application. Then, the technician will peel the backing from the top two adhesive areas 2, as previously explained. The technician then gently pulls on each support leg 4, towards the patient's chest. The technician will make sure that the penis is left exposed in the region of the cutout segment 3, to provide for the functionality of the drape, for cystoscopy access. Once the scrotum has been lifted from obscuring the perineum, and provides suitable exposure, then the technician sticks and adheres the adhesive areas 2 to the surface of the abdomen, to assure continuing clearance for medical analysis and treatment, and the application of the type of instrumentation as previously explained. The technician then leaves the drape in place until the cystoscopy has been performed, and further in the event that the physician and surgeon must have sustained access to the perineal area for further medical treatment, as previously reviewed.

Variations or modifications to the subject matter of this invention may occur to those skilled in the art upon reviewing the disclosure as provided herein. Such variations or modifications within the scope of this development, are intended to be encompassed within the subject matter of this invention. The description of the preferred embodiment provided herein is done so for illustrative purposes only.

Having thus described the invention, what is claimed and desired to be secured by Letters Patent is:

1. In the method of usage and application of the scrotal drape and support of the type including a base portion having a pair of upwardly extending legs, said upwardly extending legs and base portion having an application of pressure sensitive adhesive, including locating the base portion of the support under the scrotum of the patient during prostate examination and treatment, arranging and pulling the leg portions upwardly in order to lift the scrotum and penis upwardly during prostate examination, and adhering the upper end of the legs of the drape through the pressure sensitive adhesive to the abdomen of the patient during said treatment.

2. A scrotal drape and support for use in the examination and treatment of the prostate including said drape having a base portion, a pair of legs extending substantially upwardly from said base portion, and said pair of legs extending substantially angularly outwardly from said base portion, there being a spacing provided intermediate each of the legs, each leg having an upper tab end, each upper tab end of each leg having a pressure sensitive adhesive applied thereto, so that the drape can be applied against the abdomen of the patient and adhered thereto during usage, the base portion of the drape having an additional pressure sensitive adhesive region located in its downward portion, and which region is applied under the scrotum of the patient during prostate examination and treatment so as to locate and hold the scrotum and penis of the patient upwardly during treatment, there being covering material overlying the regions of the said adhesive to protect against exposure of the adhesive prior to usage of the said support, the covering material capable of being peeled from the support prior to its usage and application upon the patient, the base and leg portions of the drape being V-shaped in design, and said covering material being formed of one of paper, glassine, and the like.

* * * * *